US008252346B2

(12) United States Patent
Zuniga Navarro et al.

(10) Patent No.: US 8,252,346 B2
(45) Date of Patent: Aug. 28, 2012

(54) NATURAL EXTRACT FOR THE CONTROL OF BOTRYTIS CINEREA AT PRE- AND POST-HARVEST

(75) Inventors: Gustavo Zuniga Navarro, Santiago (CL); Alejandra Rivera Fonseca, Santiago (CL); Milena Cotoras Tadic, Santiago (CL)

(73) Assignee: Universidad de Santiago de Chile, Santiago (CL)

( * ) Notice: Subject to any disclaimer, the term of this patent is extended or adjusted under 35 U.S.C. 154(b) by 80 days.

(21) Appl. No.: 12/415,802

(22) Filed: Mar. 31, 2009

(65) Prior Publication Data

US 2009/0280201 A1 Nov. 12, 2009

(30) Foreign Application Priority Data

Mar. 31, 2008 (CL) ..................................... 934-2008

(51) Int. Cl.
*A01N 65/00* (2009.01)
(52) U.S. Cl. ...................................................... 424/725
(58) Field of Classification Search ........................ None
See application file for complete search history.

(56) References Cited

U.S. PATENT DOCUMENTS

| 4,933,371 | A | | 6/1990 | Hink et al. | |
|---|---|---|---|---|---|
| 5,518,722 | A | * | 5/1996 | Szaloki et al. | 424/401 |
| 7,160,706 | B2 | | 1/2007 | Tisserat | |
| 2005/0074508 | A1 | | 4/2005 | San Martin | |
| 2005/0163815 | A1 | * | 7/2005 | Bowen et al. | 424/410 |
| 2006/0121126 | A1 | | 6/2006 | McFadden et al. | |
| 2007/0125659 | A1 | * | 6/2007 | Hecker Cartes | 205/341 |

FOREIGN PATENT DOCUMENTS

| CL | 00625-1995 | | 3/1996 |
|---|---|---|---|
| CL | 01203-1998 | | 12/1998 |
| CL | 02573-2002 | | 10/2003 |
| EP | 1 867 230 A2 | | 12/2007 |
| WO | WO 2004002504 | * | 1/2004 |
| WO | WO 2007/046680 A1 | | 4/2007 |

OTHER PUBLICATIONS

Ribera et al., World J. Microbiol. Biotechnol., 2008, 24, 1803-1811.*
Prehn et al., Bosque, 24, 2, 2003, pp, 3-12, translation.*
Dictionary of Botany, 1 page, 2003.*
Ahmad, I. et al., Antimocrobial and phytochemical studies on 45 Indian medicinal plants against multi-drug resistant human pathogens, Journal of Ethnopharmacology, Vol. 74, 2001, pp. 113-123 (11 pages).
Apablaza, G. et al., Observación microscópica del efecto de control de un extracto de quillay sobre oidio de cucurbitaceas, Fitopatologia, Vol. 39, No. 3, 2004, pp. 144-149, (1 page Engilsh Abstract-only).
Apablaza, G. et al., Control de Oidio Cucurbitaceas con Saponinas Presentes En Extractos de Quillay (*Quillaja saponaria*), Cien. Inv. Agr., Vol. 29, No. 2, 2002, pp. 83-90 (8 pages with English Abstract).
Chapagain, B.P., et al., *In vitro* study of the antifungal activity of saponin-rich extracts against prevalent phytopathogenic fungi, Industrial Crops and Products, Vol. 26, 2007, pp. 109-115 (7 pages).
Inderjit, et al., On Laboratory Bioassays in Allelopathy, The Botanical Review, Vol. 61, No. 1, Jan.-Mar. 1995, pp. 28-44 (17 pages).
Moya, E. et al, El Oídío: Un amenaza creciente en al producción de pimiento en la Zona Central, Agronomía y Forestal, 2003, pp. 18-21 (1 page English Abstract-only).
Inyang, E.N. et al., The effects of isothiocyanates on the growth of the entomopathogenic fungus *Metarhisium anisopliau* and its infection of the mustard beetle, Mycological Research, Vol. 103, No. 8, 1999, pp. 974-980 (7 pages).
Kite, G.C. et al., Metabolomic analysis of saponins in crude extracts of *Quillaja saponaria* by liquid chromatography/mass spectrometry for product authentication, Rapid Commun. Mass Spectrom., Vol. 18, 2004, pp. 2859-2870 (12 pages).
Murashige, T. et al., A revised medium for Rapid Growth and Bio Assays with Tobacco Tissue Cultures, Physiol. Plant., Vol. 15, 1962, pp. 473-497 (26 pages).
Oleszek, W. et al., High-performance liquid chromatography of alfalfa root saponins, Journal of Chromatography, Vol. 519, 1990, pp. 109-116 (8 pages).
Osbourn, A.E., Preformed Antimicrobial Compounds and Plant Defense against Fungal Attack, The Plant Cell, Vol. 8, Oct. 1996, pp. 1821-1831 (11 pages).
Prehn, D. et al., Micropropagation of *Quillaja saponaria* Mol. starting from seed, Bosque (Valdvia), Vol. 24, No. 2, 2003, pp. 3-12 (11 pages with English Abstract as submitted).
Vega, A. et al., In Vitro Initiation and Early Maturation of EmbryogenicTtissue of *Quillaja Saponaria*, Cien. Inv. Agr., Vol. 32, No. 3, Dec. 2005, pp. 156-166 (11 pages).
Villegas, I., Uso de los extractos de quillay como biopesticidas y estimulantes de crecimientos. Tesis de Ingeniero Civil, Facultad de Ingenieria Civil, Pontificia Universedad Católica de Chile, 1999, 134 p. (1 page Engilsh Abstract-only).

* cited by examiner

*Primary Examiner* — Michael V Meller
(74) *Attorney, Agent, or Firm* — Daniel F. Nesbitt; Hasse & Nesbitt LLC (57) ABSTRACT

Obtaining, producing and using metabolites having anti-botrytis cinerea properties from a natural extract of a native Chilean plant. An in vitro cultivated quillay extract (*Quillaza saponaria* Mol.), which allows improving the antifungal activity as the result of the enrichment of some secondary metabolites not found in the in vivo plants. Also provided are an in vivo cultivation method, an extraction method, a biocide formulation, and their applications and uses.

20 Claims, 8 Drawing Sheets
(3 of 8 Drawing Sheet(s) Filed in Color)

| Compound | Retention time (min) | Area (mAu*s) | Content (mg/ml) |
|---|---|---|---|
| Shikimic acid | 1,296 | 136,3 | 0,79 |
| Chlorogenic acid | 4,745 | 323,2 | 0,25 |
| Esculetine | 5,235 | 104,5 | 0,14 |
| Caffeic acid | 5,240 | 175,8 | 0,29 |
| Rutine | 5,713 | 915,8 | 0,009 |
| p-Coumaric acid | 5,845 | 261,9 | 0,007 |
| Scopoletine | 6,022 | 354,5 | 0,33 |
| Vanillic acid | 6,855 | 142,6 | 0,25 |
| Salycilic acid | 7,536 | 200,2 | 0,94 |
| Quercetine | 8,403 | 479 | 0,006 |
| Naringenine | 10,01 | 106,7 | 0.004 |
| Total | | | 3,016 |

NATURAL EXTRACT FOR THE CONTROL OF BOTRYTIS CINEREA AT PRE- AND POST-HARVEST

FIELD OF THE INVENTION

This invention relates to the obtainment, production and use of metabolites with anti-botrytis cinerea properties from natural extracts of plants, including those native to Chile. The extract developed may be used to control the fungus both under pro- and post-harvest conditions.

BACKGROUND OF THE INVENTION

Fungicides are chemical compounds commonly used to control the fungi affecting cultures mainly.

Many of these compounds are organic synthetic substances with a wide range of toxicity and are persistent in the environment. Thousands of tons of fungicides are annually applied worldwide to control various fungi.

The *B. cinerea* fungus is responsible for grey rot and it may attack over 200 species of cultivated plants, especially those growing in a greenhouse. This is a saprofite fungus that attacks dead or senescent tissues, penetrates the tissue and causes the plant's death, thus resulting in huge losses to farmers. The control of this fungus is performed through chemical agents. At present, benomil and iprodione are used, but will be taken from the market, since they have developed resistance in the fungus.

An additional problem with fungicides currently being used is that their concentration must be increased in order to control the pathogen, which causes problems both in the environment and in the organisms in contact with the chemical agent. Therefore, new products are required should be highly effective and have low environmental toxicity.

As an alternative to synthetic agents, botanical pesticides have the advantage of being natural compounds, and thus are safer for humans and the environment. Specifically, botanical pesticides are less toxic than conventional pesticides and they generally affect the target organism only or those closely related thereto. Also they decay rapidly in the soil, and thus are ideal components for Integrated Pests Management (IPM) programs.

Quillay (*Quillaja saponaria* Molina) is a tree of the Rosaceae family, native to Chile, and its biomass contains molecules called saponins, specifically of the triterpenoid type. The saponins provide the extracts of this tree with unique characteristics, which have been used for decades in the various industries, such as foodstuff and drinks, mining, agriculture, animal feeding, and treatment of effluents, among others.

The main properties of the quillay extracts are: reduction of surface tension, formation of a persistent foam, and emulsification of fats and oils. There is a great amount of scientific literature (papers and patents) that describe the use of these extracts for different industrial applications. U.S. Pat. No. 4,933,371, incorporated herein by reference, describes the use of saponins of different plants (e.g. yucca, quillay, agave, and tobacco) as acaricide.

Quillay's biocide activity has been previously described for instance in Apablaza et al (Fitopatologia, Vol. 39, No 3, 2004, pages. 144-149, ISSN 0430-6155), where experiments are described about the control of cucurbitaceae oidium [Erysiphe cichoracearum DC. ex Mérat and *Sphaerotheca fuliginea* (Schlecht ex Fr.) Poll] with the saponin-containing quillay extracts (Quillaja saponaria Mol.) QL 1000 and QL 30B. The experiments provided satisfactory results in cucumber and pumpkins. In ill leaves treated with these extracts, a color change of oidium was noted, from white to brown. With the aid of a magnifying glass or microscope, disorganization of the mycelium in relation to the control was noted. The purpose of this study was to prove and observe the effect of the QL 1000 extract on the mycelium and fungus conidia under a light microscope. Pumpkin plants infected with oidium were treated with three doses of the product. Treated and control leaves were taken and they were subject to sheet scraping and microscopic observation. Tissue cuts were observed. The results of the experiments, both under the sheet scraping technique and tissue cuts, showed full chains of oidium normal conidia and conidiophore in the control leaves; partially affected and shorter chains at the 50 ppm dose of saponins; fully disorganized chains and conidia at lysis at the 100 ppm dose; and short, partially disorganized chains at the 200 ppm dose of saponins. These results allowed proving the oidium control with quillay QL-100. It should be noted in this respect that BASF QL products correspond to a 100% natural quillay-based extract nematicide, especially indicated for the control of nematodes in vineyards and citric trees.

In the EP publication 1867230, incorporated herein by reference, a natural product is described recording the anti-fungal and growth promoting effect in order to improve the productivity of plants, which comprises at least two active substances derived from a) quillay (*Quillaja saponaria*), b) quinoa (*Chenopodium quinoa*), c) tea (*Camellia* spp., e.g. *Camellia oliefera, Camellia sinensis, Camellia chekiangoleosa, C. drupifera, C. reticulata* or *C. japonica*), and d) a saponin contained in a plant material other than (a), (b) or (c).

In the international patent publication WO2007/04680, incorporated herein by reference, an organic insecticide blend is described for the control of *Aedes aegypti*, comprising extracts from *Quillaja saponaria, Chrysanthemum cinerariaefolium (pyrethrins), Azadirachta indica, Azadirachtin*, and a garlic waterish extract (*Allium* spp).

US Patent Publication US2006/121126, incorporated herein by reference, describes a composition containing an oxygen peroxide generating compound and saponin glucoside compounds, which by being combined show an increased activity against bugs, pathogens, algae, moulds and fungal activity.

A great number of patent documents have been found, which describe the use of quillay, the taking of extracts are taken, and its applications, such as CL 625-1995 application, incorporated herein by reference, where a procedure is described to produce white-colored saponins from quillay wood; CL publication 1203-1998, incorporated herein by reference, that discloses a saponin production process using quillay wood as raw material by soaking and then pressing or laminating the pre-sized wood; CL publication 2573-2002, incorporated herein by reference, that provides a production process for high-purity quillay extract based on the use of the whole biomass, comprising chipping the wood, extracting the solids, purifying the extract, filtering the blend, and concentrating the extract at the filtering and pasteurizing stage, CL publication 2772-2002, which is equivalent to US Application Publication 2005/074508, incorporated herein by reference, that describes a product for the control of phytoparasitary nematodes prepared on the basis of a waterish extract of quillaja saponaria Molina (quillay) containing both the saponin fraction and the non-saponin fraction; and the method to control nematodes where the product is applied in farming crops. These documents mainly aim at the use of saponins and in particular to the waterish fraction of the extract, always from natural sources and in vivo cultures.

The use of plants as the source of substances with biological activity requires biomass to be available, which does not always allow keeping the balance between the production and use, thus overexploitation situations of the product occurring. Also, the chemical composition of plants is strongly affected by the environment where they develop and grow, this being a problem when using them as a source for the production of active principles. This is why the development of methodologies is required allowing the sustainable use of natural resources.

The use of the in vitro culture technique of vegetal tissues in order to obtain active extracts is already known in the previous art.

The U.S. Pat. No. 7,160,706, incorporated herein by reference, describes the use of this technique in order to obtain secondary metabolites-enriched material. More specifically, under this patent, work is done to obtain alkaloids from *Papaver* sp. plants.

Although the in vitro cultivation of quillay has been described in the state of art from seeds and through somatic embryogenesis (Vega A y Prehn D (2005) "Inducción e inicio de maduración in vitro de tejido embriogénico de *Quillaja saponaria*", Ciencia e Investigación Agraria 32(3):197-207), this is first report where axillary shoots (or buds) of adult trees are used.

SUMMARY OF THE INVENTION

The present invention relates to a biocide product comprising a natural extract of at least one native Chilean plant, preferably of Quillay (*Quillaja saponaria* Mol.). In a preferred embodiment of the invention, the biocide product is enriched with bioactive metabolites from the plant, wherein the biocide product shows antifungal properties. The biocide product is useful for the control of *Botrytis cinerea* pre- and post-harvest.

In another embodiment, the invention relates to a process to obtain extracts of at least a native Chilean plant, preferably to generate an extract of Quillay (*Quillaja saponaria* Mol). In a preferred embodiment, the process allows obtaining an extract enriched in bioactive metabolites of the plant.

In an additional embodiment, the invention relates to a process to generate plants enriched with bioactive metabolites compared with plants growing in vivo under natural and wild conditions, wherein the parts of the plant are used to obtain extracts enriched with bioactive metabolites with antifungal activity. This process comprises a methodology for the production of antifungal extracts by in vitro culture, and overproduction of bioactive metabolites by using biosynthesis promoters (elicitors, biotic and abiotic agents).

In a further embodiment, the invention relates to a process or method for the pre- and post-harvest treatment of plants and fruits, their derivatives, plantations, lands and environment against fungi, preferably against *B. cinerea*.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 2 shows the effect of Quillay extracts in the radial growth of *B. cinerea* mycelium using the dilution method in a solid medium using agar extract soft yeast-malt as substratum. The culture medium with or without extracts was poured into petri plates and inoculated with *B. cinerea* at the plate center. Cultures were incubated at 22° C. in dark conditions. The mycelium diameter was daily measured with a rule. Results were expressed as a percentage of inhibition through the formula $[(C-T)/C*100]$ where C and T corresponded to the hyphal extension (cm) in the control and treated cultures, respectively. Extracts were prepared through maceration and diffusion techniques. In the former, the tissue was crushed in liquid nitrogen using ceramic mortar and pestle prior to the waterish or hydroalcoholic extraction (ethanol 85% v/v) cold, for 15 min in dark conditions. For the diffusion extraction, the vegetal material cut in small pieces was kept in touch with the cold solvent (4° C.), for 24 hours under dark conditions. Before its use, the extracts were filtered and homogenized by stirring.

FIG. 3 shows the effect of different concentrations for the ethanolic extract of quillay shoots in vitro on the germination of *B. cinerea* Pers conidia. The solvent (85% ethanol) was used as control. Both in the control and in the treatments, the ethanol concentration was the same. The trial was conducted in the culture medium agar extract soft yeast-malt supplemented with quillay's ethanolic extract at final concentrations of 0.5; 1.0 and 1.5% p/v. The culture medium was inoculated with dry conidia extracted from a sporulated culture. They were incubated inside humid chambers and incubated at 22° C. for 11 hours. The germination of conidia was directly determined at intervals of hours observing the samples under an Optical Microscope. Only the conidia with a germinative tube equal to or above the conidial diameter were considered as germinated (Inyang et al, 1999). Results were expressed as a percentage of germinated conidia through the formula $[(T*(100)/C]$, where C and T corresponded to the number of conidia germinated at the control and treated cultures, respectively.

FIG. 4 shows the effect of the ethanolic extract of quillay in vitro shoots on the ability of *B. cinerea* of colonizing tomato leaves. In the chart for (A), the injury area is depicted (cm$^2$) in the fruits treated as determined in the fifth day of incubation. The results represent the average of 10 determinations+1 standard deviation (SD). Different letters in the bars indicate that the averages are significantly different (Tukey, p<0.05). The treatments applied were: (I) Control—BC 1000 (distilled water); (II) BC 1000 (natural organic fungicide); (III) Control—extract (ethanol 8.5% v/v) and (IV)) Quillay ethanolic extract (250 µg ml-1). In the photographs for (B) the rhea growth of the pathogen can be noted in the treated leaves after 7-day incubation.

FIG. 6 shows the effect of in vitro and in vivo quillay extracts on the mycelium growth of *B. cinerea* Pers. The extracts (waterish and ethanolic) were evaluated at final concentrations of 1.0% p/v. In vitro plants after 2 months of subcultivation and in vivo plants of at least 3 years were used. The respective solvents were used as control. The inhibition percentages were calculated at the fifth day of incubation. Each bar represents the average of three independent experiments+DE. Different letters in the bars indicate that the averages are significantly different (Tukey, $p<0.05$).

DETAILED DESCRIPTION OF THE INVENTION

The present invention relates to a natural extract of at least one native Chilean plant, preferably an extract of Quillay (*Quillaza saponaria* Mol.). The extract is obtained from in vitro cultivated plants. In a preferred embodiment of the invention, said extracts comprise an ethanolic fraction of said plants, where said extract or biocide product is rich in bioactive metabolites from said plant. Preferably, the biocide product shows antifungal properties, and is preferably used for the control of *Botrytis cinerea* in pre- and post-harvest (before and after harvest).

Saponins have been reported as showing antifungal activity (Oleszek et al., 1990; Osbourn et al., 1996; Villegas, 1999; Apablaza et al., 2002; Moya, 2003; Chapagain et al., 2007). Also in the state of the art it is described that quillay metabolic extracts have more than 100 saponins (Geoffrey C. Kite et al. Metabolic analysis of saponins in crude extracts of *Quillaja saponaria* by liquid chromatography/mass spectrometry for product authentication. Rapid Commun. Mass Spectrom. 2004; 18: 2859-2870), but a description is not given for the profile of other additional metabolites to saponins as those disclosed in the present invention that contribute advantageous qualities to the extract's antifungal activity. The extract of the invention, indeed, has quantitative advantages, since on the one hand it is rich in metabolites of interest that are not obtained at an equivalent rate from extracts of wild plants. On the other hand, obtaining an extract on a continuous, stable and reproducible basis is possible, without depending on natural sources, the availability of raw material, depletion of the resource subject to seasonal variability, or modification of the extract profile for diversity of metabolites.

Figure 7:
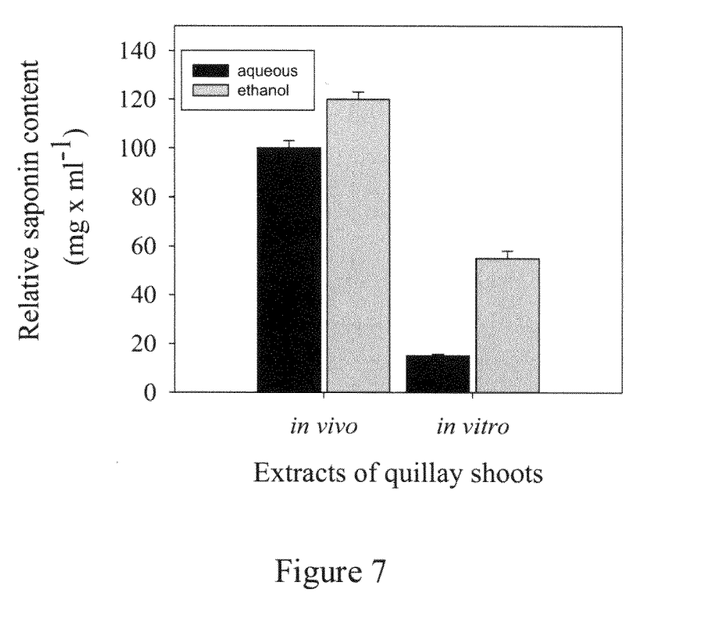
FIG. 7 shows an evaluation of saponin relative concentration in extracts of in vitro shoots and in vivo shoots of quillay. The extracts—waterish (black bars) and ethanolic (grey bars)—were evaluated at a concentration of 10% p/v. Each bar represents the average of three repetitions+DE. Different letters in the bars indicate that the averages are significantly different (Tukey, $p<0.05$).
Figure 8:
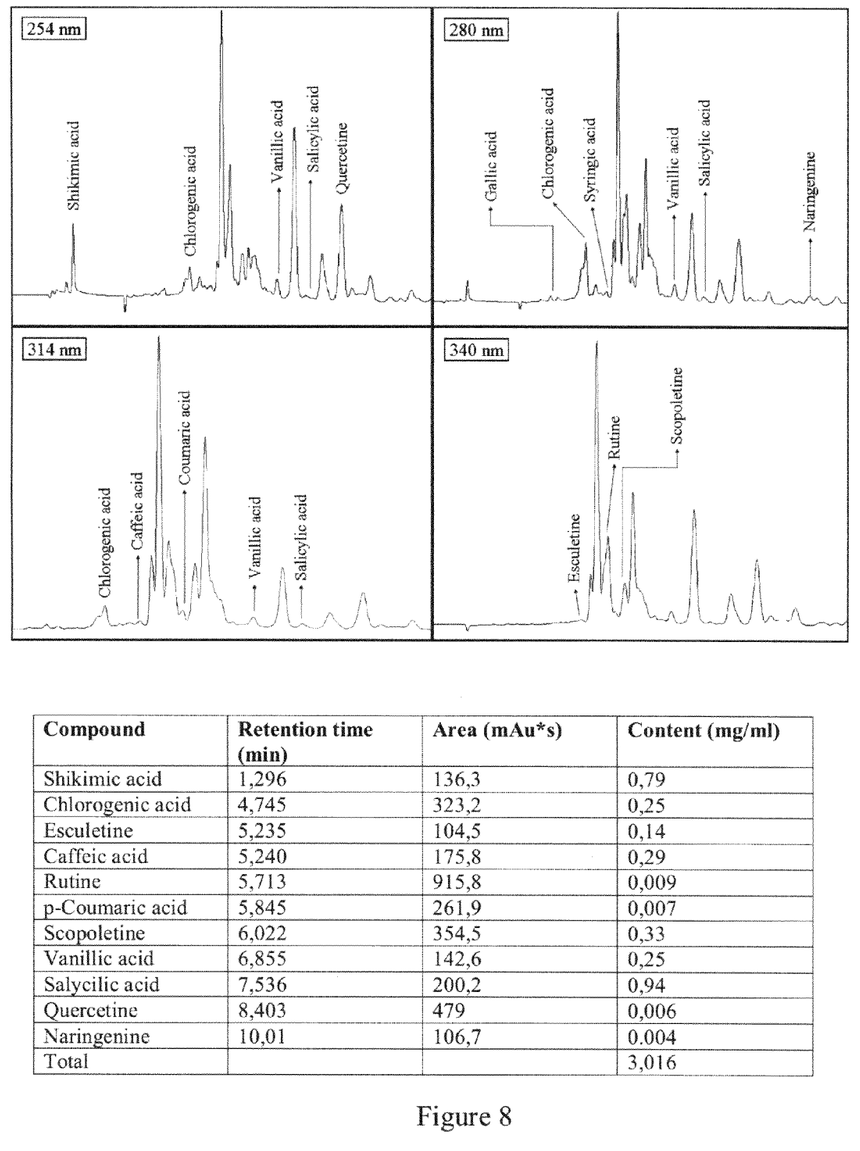
FIG. 8 shows HPLC cromatographies for the ethanolic extract of quillay in vitro cultivated shoots. The extract was injected with a 10% p/v concentration. The presence of compounds was detected at different wave lengths: 254, 280, 314 and 340 nm. The above is summed up in the table where also the retention time of each secondary metabolite and the concentration presented in the extract is indicated.
Figure 9:
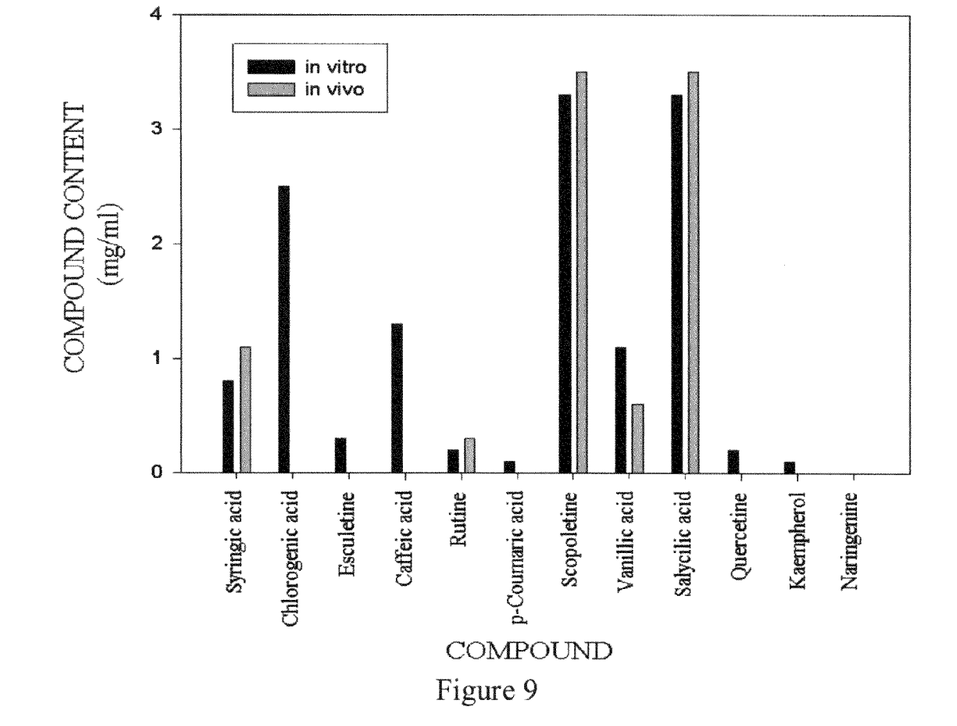
FIG. 9 shows a comparison between the quillay ethanolic extracts grown in vivo and in vitro in relation to the concentration of secondary metabolites of phenolic nature, where the existence of a different distribution of the same can be noted.
Figure 10:
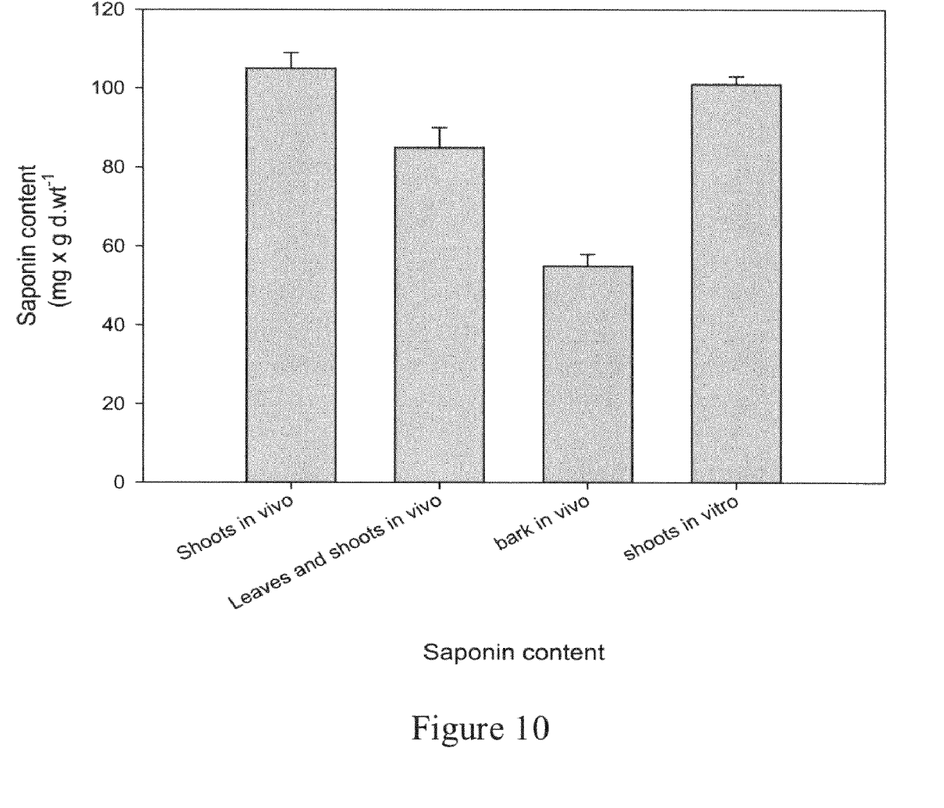
FIG. 10 shows the distribution of saponins corrected by dry weight in the quillay ethanolic extracts grown both in vivo and in vitro, where it can be noted that the concentrations for this active principle in shoots are equivalent in both cases.

The present invention shows that the relative concentration of saponins in extracts of in vitro cultivated plants is lower than that of in vivo plant extracts (FIG. 8). Hence, if the antifungal activity of extracts were the exclusive consequence of saponins, the in vitro culturivation would not be an interesting alternative. According to the above, the evidence indicated in FIG. 7 tends to show that the in vivo extracts have larger inhibition of micelar growth compared with the in vitro extracts. According to the above, the in vitro extracts do not appear to provide better activity than the in vivo equivalent extracts. It should be considered, however, that the content of dry matter of in vitro shoots is about 11%, while the content of dry matter of in vivo shoots is above 35%. It can be therefore concluded that the lower activity of the in vitro extract is due to the extract being more diluted. By correcting or normalizing to dry weight of tissue in both cases, the in vitro extract appears to be more active than its in vivo equivalent. The conclusion is that the inhibitory effect is due to the combination of different metabolic factors, with saponins being one of them, but there are other metabolites present that provide a supplement to the extract's antifungal activity and that their obtainment is possible as a result of the present invention. Indeed, FIGS. 9 and 10 show that although the presence of saponins in the extracts from the in vivo and in vitro shoots are equivalent, there is a difference in the metabolites of phenolic nature, to which the unique anti-botritys activity of the in vitro extracts can be ascribed.

The in vitro cultivation system has additional benefits, since it allows obtaining antibotrytis extract-producing vegetal biomass over periods of time much lower than that required in the traditional systems of cultivation. The method makes it possible to have a system of continuous production of quillay biomass, which does not depend on the environment, being therefore highly reproducible in terms of its antibotrytis properties. Also, the cultivation method allows reproducing and managing the better yield conditions as regards the production of antifungal activity.

Notwithstanding the above and according to an aspect of the present invention, a conclusion could be made that a combination of bioactive metabolites present in quillay, preferably phenolic compounds, allows an outstanding and novel antifungal activity to be achieved. This outstanding antifungal activity of in vitro cultivated plants may be due to the presence of a number of secondary metabolites (Table 1), for which antifungal activity for phytopathogen fungi has been reported. These analytes can be found in concentrations between 0.0005 and 2 mg ml$^{-1}$, preferably between 0.003 and 1 mg ml$^{-1}$, more preferably according to the concentration ranges indicated in Table 1.

TABLE 1

| Metabolite | Concentration Range (mg ml$^{-1}$) | Preferred Concentration (mg ml$^{-1}$) |
|---|---|---|
| Shikimic acid | 0.05-1.5 | 0.7985 |
| Chlorogenic acid | 0.05-0.5 | 0.2482 |
| Esculetine | 0.02-0.5 | 0.135 |
| Caffeic acid | 0.05-1.0 | 0.2901 |
| Rutine | 0.002-0.03 | 0.0085 |
| P-coumaric acid | 0.002-0.03 | 0.0066 |
| Scopoletin | 0.05-0.8 | 0.3313 |
| Vinillic acid | 0.05-0.5 | 0.2523 |
| Salicylic acid | 0.05-1.5 | 0.9352 |
| Quercitine | 0.002-0.03 | 0.0062 |
| Naringenine | 0.002-0.03 | 0.0036 |

In a preferred embodiment of the invention, a natural extract of in vitro cultivated plants comprises a combination of saponins and other secondary metabolites. Preferably among said secondary phenolic compounds are found, and preferably these secondary metabolites comprise, at least one metabolite selected from the shikimic acid, chlorogenic acid, esculetine, caffeic acid, rutine, p-coumaric acid, scopoletin, vinillic acid, salicylic acid, quercitine and naringenine. A preferred embodiment of the invention comprises an ethanolic extract of in vitro cultivated plants comprising saponins and all the compounds mentioned above.

In another embodiment, the invention comprises a biocide formulation or product for farming use, as a formulation that can be liquid or solid, that is ready use or is prepared by suspension, dilution, emulsion or another usual procedure in the art. This product may be applied by aspersion, bathing, immersion, as a film or other usual embodiments of the art. This product may be applied to the plant, its fruits, its environment, land, seeds, storage place or depots where the plants and their fruits are kept after harvesting them.

Figure 5:
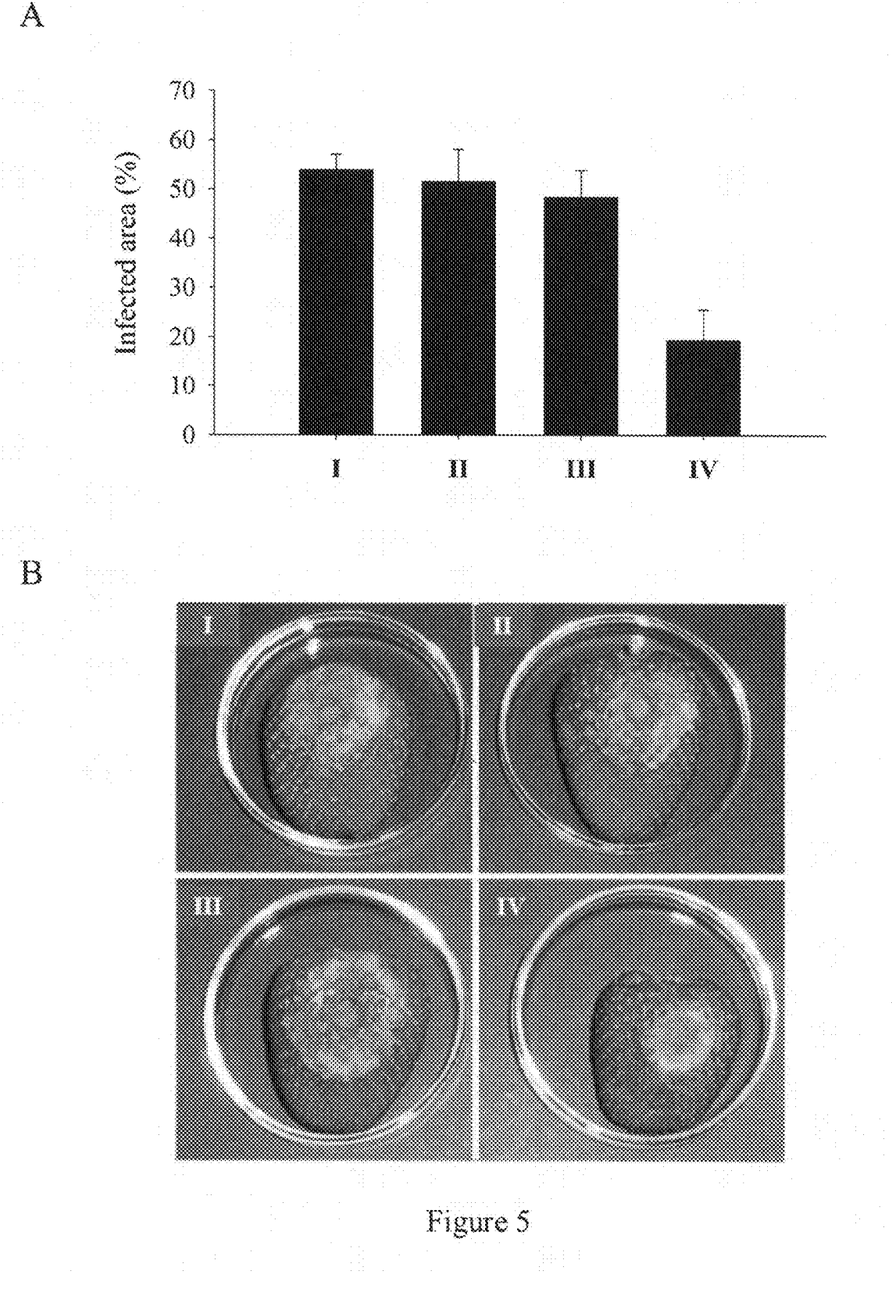
FIG. 5 shows the effect of the ethanolic extract of in vitro quillay shoots on the infection degree through *B. cinerea* in strawberries fruits. In the chart for (A), the percentage of infected area in the fruits treated is shown, calculated at the fifth day of incubation. The results represent the average of 16 determinations+DE. Different letters in the bars indicate that the averages are significantly different (Tukey, p<0.05). In the photographs for (B) the growth of *B. cincerea* is shown in fruits treated after 5 days of incubation. The treatments applied were: (I) Control—BC 1000 (distilled water); (II) BC 1000; (III) Control—extract (ethanol 8.5% v/v) and (IV) Qullay ethanolic extract of in vitro shoots (250 µg ml–1).
Figure 6:
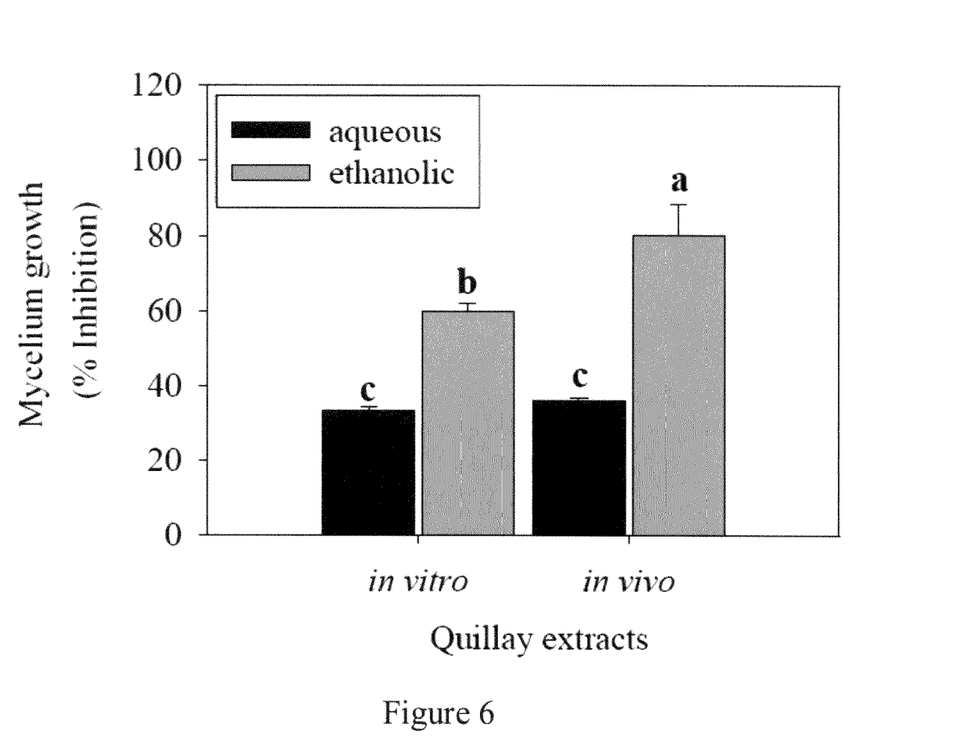

The present invention contributes to the art with an extract with different qualities than the extracts obtained from the same species of plants grown wildly in vivo (FIG. 7). Indeed, the present invention comprises a method for the in vitro cultivation of said native plants through micropropagation. The above shows huge environmental and productive advantages, since the generation of the extract does not depend on the wild sources of plants subject to variation due to climate changes, the condition of nutrients, irrigation, etc., which would prevent obtaining an extract with homogeneous characteristics in regard to its components and activity in addition to subjecting the natural resource to a possible depletion, and generating a biotechnological and viable alternative to generate a safe agrochemical agent for the control of B. cinerea, since it shows improved qualities in relation thereto (FIGS. 5 and 6).

According to the above, the present invention comprises a method to obtain extracts with antifungal activity from in vitro cultivated plants, comprising the micropropagation of plants, the cultivation under proper conditions for the induction of secondary metabolites of interest, the harvest of shoots and processing thereof in order to obtain an extract with the qualities mentioned above.

In a micropropagation embodiment, shoots of plants of about one year are disinfected and transferred to cultivation containers with a MS medium (the composition is described in Murashige & Skoog, 1962) supplemented with benzylaminopurine (0.1 to 0.5 mg/l), kinetine (0.1 to 0.5 mg/l), biotine (0.01 to 0.5 mg/l) and sacarose (10 to 50 mg/l), with an adjusted pH of 5.7 and subject to autoclave, then solidified with agar 0.8%. The micropropagation process is the usual or conventional one, notwithstanding these modifications have been incorporated in relation to a constant temperature range and a spring photoperiod, e.g. 16 hours of light and 8 hours of darkness. These cultivation conditions are the ones that could explain the differences in terms of activity and profile of metabolites provided by the in vivo extract.

According to an embodiment of the invention, a method is provided to obtain the extracts. The preparation of extracts is preferably done with young shoots, preferably not above 3 months of age. In the case of wild plants, young shoots were used for comparative trials. Preferably, the extracts were prepared with some modifications in relation to the description of Inderjit & Dakshini 1995, Ahmad & Beg, 2001. The extraction process comprises treating the vegetal material with different volumes of solvent; specifically between 5 and 20 g of fresh tissue were taken and they were extracted in 100 ml of solvent (water or ethanol 85%). Once extracted, they should be filtered, concentrated and dried in a Rotavapor to be then stored at 4° C. in darkness. The extracts could be fractioned through preparative chromatographic procedures or other methods known in the art in order to obtain an extract enriched in bioactive secondary metabolites under the invention.

The extracts obtained under the procedure above were used to generate the biocide products according to the invention and for the tests of antifungal activity to be conducted. According to the invention, the extracts or biocide products obtained are useful to treat or prevent the infestation through B. cinerea in plants, fruits, its parts and derivatives, the land, the storage place, transportation devices and means; they can be applied by aspersion, bathing, immersion, as a film or other usual embodiments of the art.

Example 1

Quillay Multiplication System

Multiplication of seedlings: A system of in vitro cultivation of quillay was implemented from axillary leave shoots. Optimization of disinfection methods for explants and the formulation of the cultivation medium allowed the proper development of the shoot micropropagation stage.

Explants were transplanted for 15 days in a MS substrate, to which the following was added: myoinositol (100 mg/L), glycine, thiamine (1 mg/L), PVP (to reduce the formation of compounds deriving from the oxidation of phenols), sacarose (20 g/L) and agar (7.5 g/L); then the pH was adjusted to a value of 5.5 by using KOH or HCl 0.1 to 1 N prior to autoclaving at 120° C. for 20 minutes. The agar was mixed with the cultivation medium in order to obtain its solidification, and then the suspension was stirred and heated to a temperature of about 90° C. About 20 ml of substratum were transferred to the inside of 200 mL cultivation bottles, covered with aluminum foil, and then to be sterilized in an autoclave at 120° C. for 20 minutes. The transfer of cultivations to containers was done under sterile conditions—under a laminar flow chamber—using pliers and scalpels previously sterilized under a burner. Cultivations were kept in growth chambers with a photoperiod of 16/24 hours, luminous intensity of 40 micromoles×m2×sec and temperature of 22-24° C.

The cultivation medium was a Murashige and Skoog cultivation medium (MS).

| Nutrient | Mg/liter |
| --- | --- |
| $NH_4NO_3$ | 1650 |
| $H_3BO_3$ | 6.2 |
| $CaCL_2$ | 332.2 |
| $CoCL_2*6H_2O$ | 0.025 |
| $CuSO_4*5H_2O$ | 0.025 |
| $Na_2EDTA*2H_2O$ | 37.26 |
| $FeSO_4*7H_2O$ | 27.8 |
| $MgSO_4$ | 180.7 |
| $MnSO_4$ | 16.9 |
| $Na_2MoO_4$ | 0.25 |
| KI | 0.83 |
| $KNO_3$ | 1900 |
| $KH_2PO_4$ | 170 |
| $ZnSO_4*7H_2O$ | 8.6 |
| Glycine | 2 |
| Myo-Inositol | 100 |
| Nicotinic acid | 0.5 |
| Thiamine*Hcl | 0.1 |
| Sacarose | 25000 |
| Agar | 8000 |
| PH | 5.8 |

For the quillay cultivation, the cultivation medium was supplemented with BAP (0.3 mg/L, benzyl-amino purine), kinetine (0.3 mg/L) and biotine (0.1 mg/L).

Cultivations are kept in a cultivation chamber at a constant temperature of 21±2° under fluorescent tubes at an intensity of 65 umol m−2 s−1 and a photoperiod of 16 hours of light.

The methodology used is efficient, since it shows a Multiplication Index equal to 5, this meaning that from 1 shoot an average of 5 shoots is obtained after 1-month cultivation. After one month cultivation, the production of shoots with 6-7 internodes of 7-8 cm high with an average dry matter value of 11% was achieved, which is considered proper for in vitro cultivated plants. For the replication of plants, side shoots were used from 2 to 3 shoots of plants cultivated for one month.

Example 2

Obtainment of Extracts and Evaluation of the Activity

For the obtainment of vegetal extracts, fresh quillay shoots were used after 1 month of in vitro sub-cultivation, as described in the example 1; for the extracts from plants under natural conditions of growth (in vivo conditions), new leaves were used (fresh tissue) of adult specimens, obtained from the Mahuida Parque located at the "Precordillera" area, Metropolitan Region, Chile. The extracts of in vitro shoots were prepared by immersing 5, 10 and 15 g of tissue in 100 ml of solvent (5, 10 or 15% p/v), while the extracts of in vivo plants were prepared only at a 10% p/v concentration.

The extracts were prepared through maceration and diffusion techniques. Under the former, the tissue was crushed in liquid nitrogen using ceramic mortar and pestle prior to the waterish or hydroalcoholic extraction (ethanol 85% v/v) cold, for 15 min in dark conditions. For the diffusion extraction, the vegetal material cut in small pieces was kept in touch with the cold solvent (4° C.), for 24 hours under dark conditions. Before its use, the extracts were filtered and homogenized by stirring.

Antifungal Activity of Quillay Extracts

Figure 1:
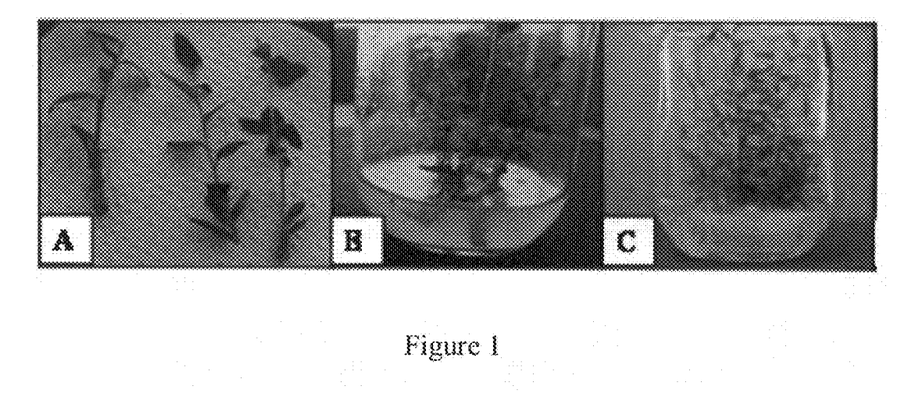
FIG. 1 shows the micropropagation sequence of Quillay plants: (A) Micropropagation explants, (B) Multiplication of explants, (C) 1-month incubation shoots (or buds, known in Spanish as "brotes") in a Murashige and Skoog medium, which were cultivated in a cultivation chamber at a steady temperature of 21±2° under fluorescent tubes at an intensity of 65 umol m$^{-2}$ s$^{-1}$ and a photoperiod of 16 hours of light. For plants to be replicated, side shoots of plants cultivated for 1 month were used.
Figure 2:
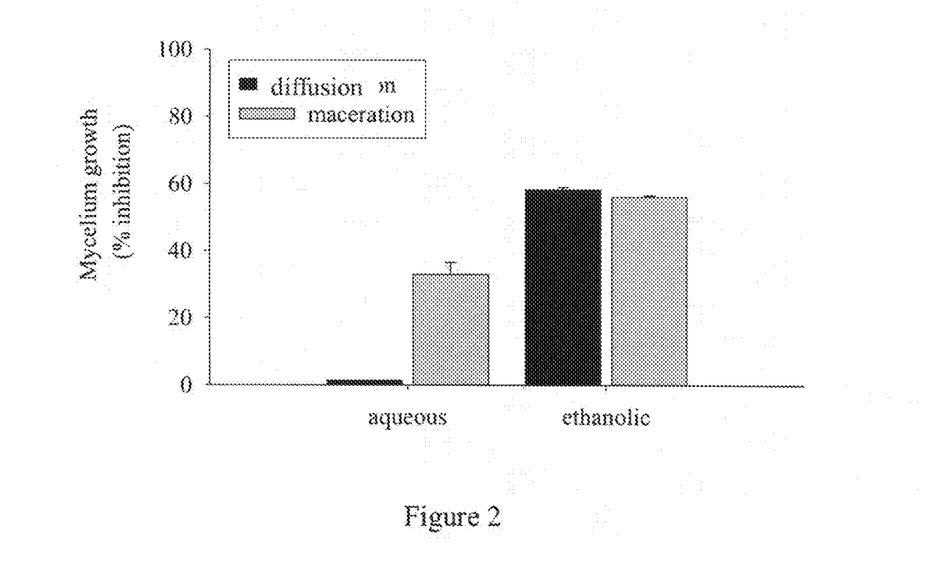
Figure 3:
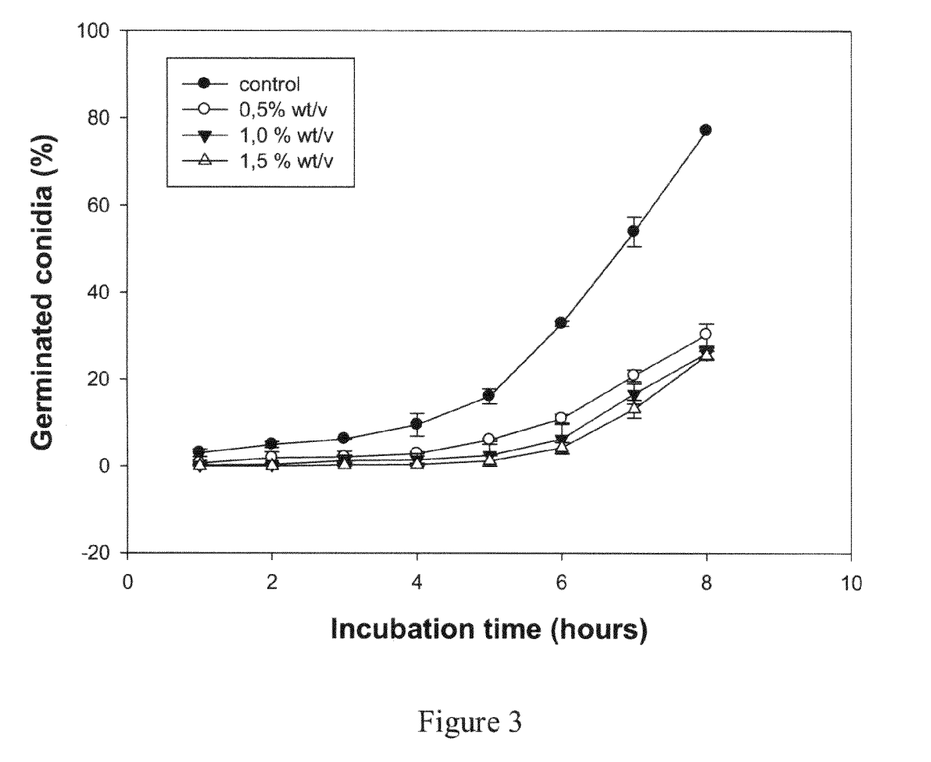

The effect of extracts on the radial growth of mycelium using the dilution method in a solid medium using agar extract soft yeast-malt as substratum was studied. Based on this, aliquots from the extracts were added at concentrations of 5, 10 and 15% p/v or the solvent as control, in a 1:10 proportion to the cultivation medium before the gellification of the cultivation medium. Thus, the extracts were evaluated at the final concentrations of 0.5, 1.0 and 1.5% p/v. The final concentration of the solvent was identical in the control and the treatments. The cultivation medium with or without extracts was poured into 9 cm diameter Petri plates. The plates were placed in a laminar flow chamber for 30 minutes for the solvent evaporation and then inoculated with 0-5 cm disks of B. cinerea fine mycelium after 72 hours of growth; these were placed at the plate center following a reversed order. Cultivations were incubated at 22° C. in dark conditions. The mycelium diameter was daily measured with a rule. The antifungal activity can be noted at FIGS. 2 and 3, where the results were expressed as a percentage of inhibition through the formula [(C−T)/C*100] where C and T corresponded to the hyphal extension (cm) in the control and treated cultivations, respectively.

Example 3

Effect of Quillay Extracts on the Germination of Conidia

Figure 4:
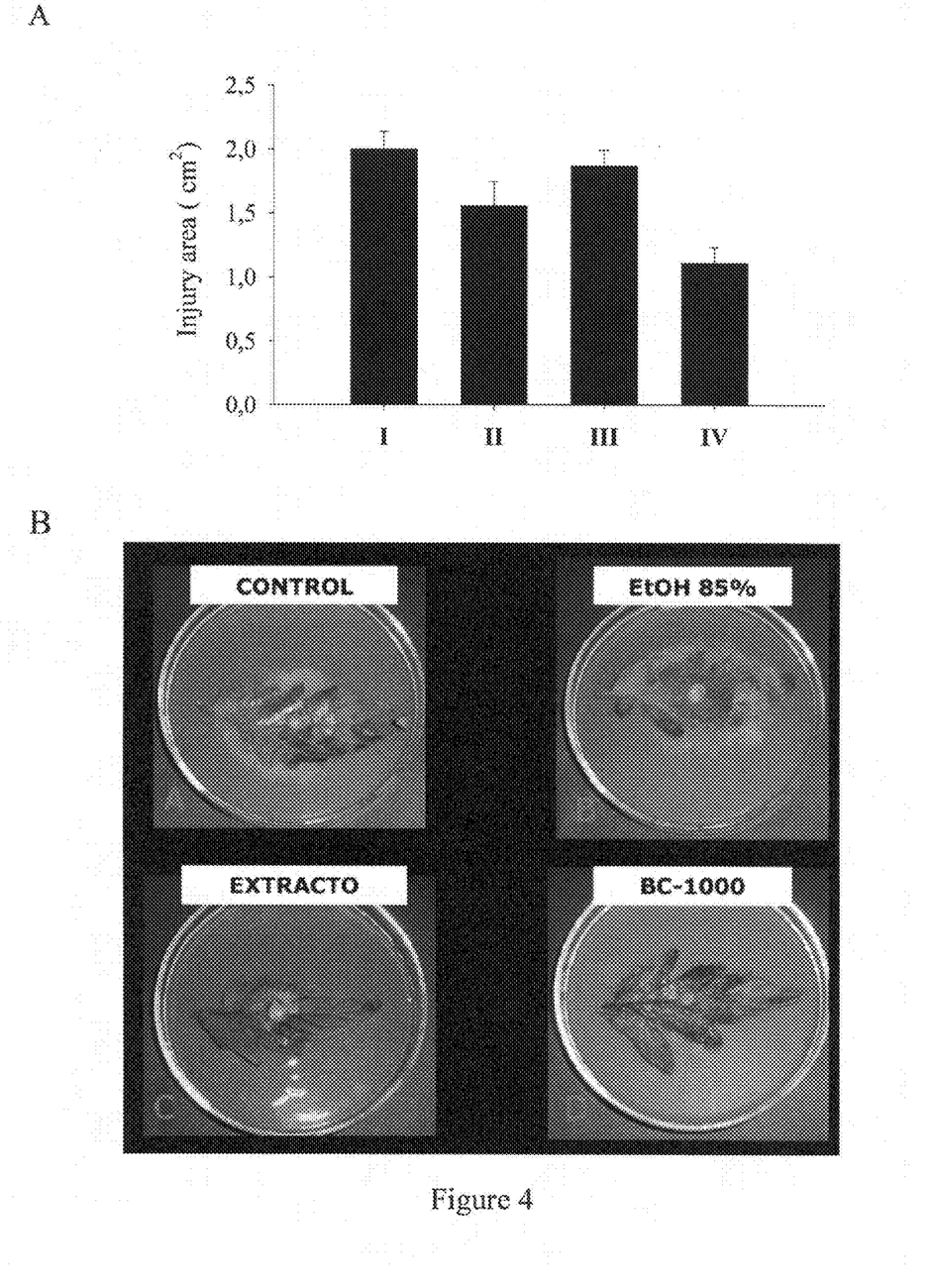

The trial was conducted in microscope slides, to which effect 5 ml of the cultivation medium agar extract soft yeast-malt were placed, supplemented with the ethanolic extract of quillay in vitro shoots at final concentrations of 0.5, 1.0 and 1.5% p/v or the solvent as control. After the evaporation of the solvent and gellification of the cultivation medium, the slides were inoculated with dry conidia by delicately spreading on the cultivation medium a piece of agar taken from the esporulated cultivation after 10 days of incubation (22° C. in dark conditions). After the inoculation, the slides were placed inside humid chambers and incubated at 22° C. for 11 hours. The germination of conidia was directly determined in the slides at the intervals of hours observing the samples with an Optical Microscope. Only those conidia with a germinative tube equal to or above the conidial diameter were considered germinated (Inyang et al., 1999). The effects are shown in FIG. 4, where the results were expressed as a percentage of conidia germinated by the formula [(T*(100)/C], where C and T corresponded to the number of conidia germinated in the control and treated cultivations, respectively.

Example 4

In Vivo Antifungal Activity in B. cinerea of In Vitro Quillay Extracts

The ethanolic extract (ethanol 85% v/v) was diluted 10 times in distilled water in order to set the fungistatic effect of the solvent aside, and used under a concentration close to, but above $ED_{50}$ thereof (according to the results obtained in the in vitro trials). The final concentration of the solvent was identical for control and treatments. As positive control, the commercial fungicide of vegetal origin BC1000 was used. The average value of 3 independent experiments was used for the calculations.

Ability of B. cinerea to Colonize Tomato Leaves (FIG. 4).

Tomato leaves harvested (L. esculentum Mill.) cv. Roma, were disinfected with 10% v/v sodium hypochlorite (10 min under stirring), three times washed with sterile distilled water, placed on absorbing paper in order to eliminate the excess water and arranged on the center of Petri plates containing agar-water (agar 1% p/v). Then, on the surface of the leaves the ethanolic extract of in vitro quillay shoots (250 μg ml−1) was applied with a brush, as well as ethanol 8.5% v/v (negative control of the extract), the commercial organic fungicide BC-1000 at the recommended dose (positive control of the extract) or distilled water (negative control of BC 1000). The leaves treated after the solvent evaporation were inoculated at the center with a 0.5 cm disc of fine mycelium of B. cinerea of 72 hours growth.

The plates were sealed and incubated at 22° C. (Cotoras et al., 2004). After 5-day incubation the area of the injury was measured with a rule. Ten repetitions were made by treatment.

Development of the Infection by B. cinerea in Strawberry Fruits (FIG. 5)

Strawberry (F. chilensis L.) fruits harvested of uniform size, free of decay and infection were disinfected with 10% v/v sodium hypochlorite, washed three times with sterile distilled water and placed on absorbing paper to eliminate excess water. Then, a 0.5 cm injury was made at the center of each fruit with the aid of a sterile scalpel. Fruits were sprayed with solutions of ethanolic extract of quillay in vitro shoots (250 μg ml−1), 8.5% v/v ethanol (negative control of the extract), fungicide BC-1000 (positive control of the extract) or distilled water (negative control BC 1000) and inoculated into the injury after the solvent evaporation with 30 μl of a conidia suspension of 1×106 conidia ml−1.

The inoculated fruits were incubated in a humid chamber at 22° C. (Bhaskara et al., 1988) and then after 5 days of incubation, the percentage of the fruit's infected area was determined. Sixteen repetitions were made by treatment.

Example 5

Characterization of Secondary Metabolites of Quillay Extract

The content of saponins in waterish and ethanolic extracts of in vitro shoots and in vivo leaves of quillay showed differences. In both kinds of extracts, the relative concentration of saponins in ethanolic extracts was higher than that detected in waterish extracts. According to this and to the results obtained in the evaluation of the in vitro fungitoxic activity—indicating a greater antifungal activity for ethanolic extracts—the concent of saponins and the fungitoxic effect of quillay extracts were positively correlated, with this suggesting that the antifungal activity thereof in *B. cincerea*—including those obtained from in vitro cultivated shoots—would be at least partially explained by the content of saponins (FIG. 6).

According to the above, the additional components present in the extract were evaluated, and an abundant number of compounds were found, which were identified through HPLC and shown at FIG. 8.

According to the invention, the greater antifungal activity of the extracts disclosed herein is due to the distribution and presence of the metabolites identified at Table 1 or FIG. 8, which is supported by the evidences provided at FIG. 9.

We claim:

1. A method for obtaining a quillay extract with improved antifungal activity, from in vitro-cultivated Quillay plants for use as an antifungal agent, comprising the steps of:
    generating plants by micropropagation of axillary shoots of adult quillay trees, wherein the adult quillay trees are about one year old, and wherein the shoots of the adult quillay trees are not older than about 3 months;
    harvesting one or more shoots obtained from the micropropagated plants generated, wherein the harvested shoots are not older than about one month;
    extracting the harvested shoots from the micropropagated plants with an aqueous solvent to produce a quillay solvent extract;
    filtering and concentrating the quillay solvent extract to obtain a quillay extract; and
    optionally drying the quillay extract to obtain a dried quillay extract.

2. The method for obtaining a quillay extract according to claim 1, further including the step of:
    fractionating the quillay extract via chromatography.

3. The method for obtaining a quillay extract according to claim 1, where in the extracting step, the aqueous solvent is aqueous ethanol and the proportions of harvested plant to solvent is 5-20 g harvested plants per 100 ml of solvent.

4. The method according to claim 3, wherein the step of generating plants by micropropagation includes a cultivation condition that includes a spring photoperiod.

5. The method according to claim 1, wherein the obtained quillay extract comprises a plurality of bioactive secondary metabolites that include saponin.

6. The method according to claim 5, wherein the obtained quillay extract comprises the saponin and at least one other bioactive secondary metabolite that includes a phenolic compound.

7. The method according to claim 6, wherein the phenolic compound is selected from the group consisting of shikimic acid, chlorogenic acid, esculetine, caffeic acid, rutine, p-coumaric acid, scopoletin, vinillic acid, salicylic acid, quercitine, naringenine, and mixtures thereof.

8. The method according to claim 7, wherein the phenolic compound is selected from the group consisting of scopoletin, salicylic acid, and mixtures thereof.

9. The method according to claim 1, wherein the obtained quillay extract has antifungal activity against *B. cinerea*.

10. The method according to claim 1, wherein the step of extracting comprises macerating the harvested plants prior to extracting.

11. The method according to claim 10, wherein the step of generating plants by micropropagation includes a cultivation condition that includes a spring photoperiod.

12. The method according to claim 10 wherein the aqueous solvent is an aqueous ethanol solvent.

13. The method according to claim 1, wherein the step of generating plants by micropropagation includes a cultivation condition that includes a spring photoperiod.

14. The method according to claim 1, wherein the step of extracting comprises diffusion extracting the harvested plants.

15. The method according to claim 14, wherein the step of generating plants by micropropagation includes a cultivation condition that includes a spring photoperiod.

16. The method according to claim 14 wherein the aqueous solvent is an aqueous ethanol solvent.

17. The method according to claim 1 wherein a growing medium is used for the micropropagation step, and wherein the growing medium comprises a Murashige and Skoog (MS) cultivation medium supplemented with benzyl-amino purine (BAP), kinetine, and biotine.

18. The method according to claim 17, wherein the step of generating plants by micropropagation includes a cultivation condition that includes a spring photoperiod.

19. The method according to claim 1 wherein the aqueous solvent is an aqueous ethanol solvent.

20. The method according to claim 19, further including the step of fractionating the quillay extract via chromatography.

* * * * *

UNITED STATES PATENT AND TRADEMARK OFFICE
CERTIFICATE OF CORRECTION

PATENT NO. : 8,252,346 B2
APPLICATION NO. : 12/415802
DATED : August 28, 2012
INVENTOR(S) : Gustavo Zuniga Navarro, Alejandra Ribera Fonseca and Milena Cotoras Tadic It is certified that error appears in the above-identified patent and that said Letters Patent is hereby corrected as shown below:

Title Page, Item (75) Inventors:, line 2, delete "Alejandra Rivera Fonseca" and insert
-- Alejandra Ribera Fonseca --.

Signed and Sealed this
Eighteenth Day of June, 2013

Teresa Stanek Rea
*Acting Director of the United States Patent and Trademark Office*